(12) United States Patent
Quallich et al.

(10) Patent No.: US 6,387,925 B1
(45) Date of Patent: May 14, 2002

(54) POLYMORPHS OF A CRYSTALLINE AZO-BICYCLO (2.2.2) OCT-3-YL AMINE CITRATE AND THEIR PHARMACEUTICAL COMPOSITIONS

(75) Inventors: George Joseph Quallich, North Stonington, CT (US); Lewin Theophilus Wint, Wilmette, IL (US); Peter Robert Rose, Ledyard; Stephen S. Massett, Groton, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/887,682

(22) Filed: May 12, 2000

Related U.S. Application Data

(60) Provisional application No. 60/136,995, filed on Jun. 1, 1999.

(51) Int. Cl.$^7$ ...................... A61K 31/439; C07D 453/02
(52) U.S. Cl. ........................................ 514/305; 546/133
(58) Field of Search ........................... 546/133; 514/305

(56) References Cited

U.S. PATENT DOCUMENTS 5,939,433 A * 8/1999 Ito et al. ..................... 514/305
6,262,067 B1 * 7/2001 Allen et al. ................. 514/305

* cited by examiner

Primary Examiner—Patricia L. Morris
(74) Attorney, Agent, or Firm—Peter C. Richardson; Paul H. Ginsburg; Jolene W. Appleman

(57) ABSTRACT

Two crystalline polymorphic forms of (2-Benzhydryl-1-azo-bicyclo[2.2.2]oct-3-yl)-(5-isopropyl-2-methoxybenzyl)-amine citrate monohydrate (the monohydrates) are Form A and Form B. The pharmaceutical composition containing at least one of these polymorphs has advantageous stability for formulation to treat acute emesis in patient receiving chemotherapy. The administration of this pharmaceutical composition is conventional oral by preferably tablet or capsule and intravenous. A method of making A and B Forms is also disclosed.

19 Claims, No Drawings

POLYMORPHS OF A CRYSTALLINE AZO-BICYCLO (2.2.2) OCT-3-YL AMINE CITRATE AND THEIR PHARMACEUTICAL COMPOSITIONS

This application claims benefit of provisional application, Ser. No. 60/136,995, filed Jun. 1, 1999.

BACKGROUND OF THE INVENTION

This invention is directed to certain polymorphs and forms of crystalline (2-Benzhydryl-1-azo-bicyclo[2.2.2]oct-3-yl)-(5-isopropyl-2-methoxybenzyl)-amine citrate (hereafter the citrate salt) and their pharmaceutical compositions. The citrate salt is a CNS active NK-1 receptor antagonist and this invention is directed to methods of treating conditions effected or facilitated by a decrease in substance P mediated neurotransmission. The invention is also directed to substance P antagonist which is evaluated for acute and delayed anti-emetic effacacy in a mammal including humans receiving chemotherapy. Treating is defined here as preventing and treating.

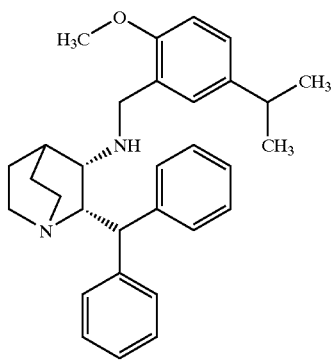

U.S. Pat. No. 5,393,762 and U.S. Ser. No. 08/816,016 both incorporated by reference, describe pharmaceutical compositions and treatment of emesis using NK-1 receptor antagonists. The crystalline anhydrous citrate salt is nonhygroscopic and exhibits a distinct X-ray powder pattern and a melt onset of 159.9° C., The anhydrous citrate was converted to the monohydrate in water.

SUMMARY OF THE INVENTION

The present invention relates to the anhydrous citrate of (2-Benzhydryl-1-azo-bicyclo[2.2.2]oct-3-yl)-(5-isopropyl-2-methoxybenzyl)-amine, the citrate monohydrate and its two polymorphs.

In one embodiment of the invention, the anhydrous citrate is a crystalline stable nonhygroscopic single form. The crystalline habits in the anhydrous citrate are microcrystalline flakes and are characterized by the x-ray powder detraction pattern below.

| Peak No. | 1 | 2 | 3 | 4 | 5 | 6 | 7 | 8 | 9 |
|---|---|---|---|---|---|---|---|---|---|
| D space | 17.61 | 10.95 | 8.78 | 7.96 | 7.37 | 6.80 | 6.57 | 5.87 | 5.46 |

In two other embodiments, the citrate monohydrate is in crystalline Forms A or B. Form A is characterized by the x-ray diffraction pattern below.

| Peak No. | 1 | 2 | 3 | 4 | 5 | 6 | 7 | 8 | 9 |
|---|---|---|---|---|---|---|---|---|---|
| D space | 17.74 | 10.93 | 9.65 | 8.25 | 6.71 | 5.98 | 5.67 | 5.45 | 4.83 |

Form A crystalline habits are birefringent needles which undergo volatilization at about 84° C., recrystallize to a lath habit and melt about 162.6° C. Form B's crystalline habits are birefringent plates, undergo volatilization at 102° C., recrystallize to less birefringent crystals characterized by melt onset of about 120° C. and recrystallize to microcrystals with melt onset of about 149° C. with degradation. Form B is characterized by the x-ray diffraction pattern below.

| Peak No. | 1 | 2 | 3 | 4 | 5 | 6 | 7 | 8 |
|---|---|---|---|---|---|---|---|---|
| D space | 12.3 | 11.3 | 6.9 | 5.9 | 4.3 | 4.1 | 3.5 | 3.2 |

Another aspect of the invention relates to a pharmaceutical composition having pharmaceutical activity which comprises at least one of polymorphic Forms A and B of the citrate monohydrate and the anhydrous citrate in the treatment of emesis. A method of treating emesis comprises administering to a subject in need of treatment an antiemetic effective amount of the polymorphic A or B Forms or the anhydrous citrate.

Polymorphic Form A of (2-Benzhydyl-1-azobicyclo[2.2.2]oct-3-yl)-(5-isoproyl-2-methoxybenzyl-amine citrate monohydrate comprises dissolving the anhydrous citrate in isopropyl alcohol and water and stirring the mixture overnight at room temperature. The citrate monohydrate salt is crystallized and Form A is collected by filtration. Form A is then dried at about 20 to 80° C. under vacuum. The synthesis is carried out for about 1.5 to 72 hours under ambient conditions. Large crystals of Form A with a plate like habit are grown from an ether/water solution and are grown with a needle like habit in acetone/diisopropyl ether/water. A method of making polymorphic Form B of the citrate monohydrate comprises concentrating a solution of the citrate monohydrate in methanol at room temperature for about 48 to 72 hours.

DETAILED DESCRIPTION OF THE INVENTION

Anhydrous citrate synthesis was carried out by adding 1.1 equivalents citric acid to a stirred slurry of the free base in isopropanol (15 volumes) at room temperature. The resulting solution was stirred and monitored by differential scanning calorimetry and after all the free base had reacted (18 hours), the anhydrous citrate salt was obtained as a white crystalline solid by filtration and drying under house vacuum at 45° C. with nitrogen purge (83% yield). X-ray powder diffraction and PLM revealed the salt to be crystalline. The crystalline habits frequently encountered are microcrystalline flakes. The most intense reflections, d spacings, observed by X-ray powder diffraction were 17.608, 10.953, 8.782, 7.956, 7.371, 6.802, 6.571, 5.866, 5.462, 4.907, 4.415, 4.188, 3.635 and 3.512Å. The crystals exhibited a melt onset at 159.8° C. with decomposition. Hygroscopicity measurements demonstrated that 1.11% wt./wt. water was absorbed at 90% RH.

A method of making crystalline citrate monohydrate, polymorphic Form A comprises the addition of a solution of 13.9 kg of citric acid (anhydrous, 99.5+%) in acetone (125 L) to a solution of 50 kg free base in isopropyl alcohol (250 L). The clear solution was filtered, stirred and the acetone removed by distillation. The resulting mixture was stirred at ambient temperature until crystallization started and then granulated for an additional 16 hours. The white crystalline anhydrous citrate which formed was collected by filtration and dried at 25° C. under vacuum (80% yield).

Anhydrous citrate, (26.4 kg) was dissolved in isopropyl alcohol (264 L), water (13.2 L) was added and the mixture stirred overnight at room temperature. The citrate monohydrate salt crystallized and was collected by filtration and dried at 25° C. under vacuum 24.9 kg product, (91.8% yield) was obtained.

The resulting citrate monohydrate salt, Form A, was compared to an authentic sample and characterized via PLM, X-ray powder diffraction, proton NMR, Karl Fisher, DSC and elemental analysis. X-ray powder diffraction and PLM revealed it to be crystalline. The two crystalline habits having similar refractograms encountered were plates and needles. The needle habit was as a result of different rate of growth of the crystal faces in water whereas in isopropanol/water more even growth of crystal faces produced plates. The most intense reflections, d spacings, observed by X-ray powder diffraction were 17.730, 10.928, 9.651, 8.253, 6.707, 5.981, 5.666, 5.450, 4.833, 4.488, and 3.646Å. The crystals exhibited a volatilization at 84° C. and a melt onset at 159.9° C. with decomposition. Hygroscopicity measurements demonstrated that 2.44% wt./wt. water was absorbed at 90% RH. Karl Fisher analysis showed the presence of 2.7% water (2.66% theoretical) verifying that the monohydrate was synthesized. Elemental analysis validated the purity of the salt synthesized.

Preparation of Form B citrate monohydrate salt was accomplished by slurrying in methanol under ambient conditions for about 1.5 to 72 hours. The product was collected by filtration. Refluxing of the citrate monohydrate salt for 18 hours gives the same results.

Form B is polymorph of the citrate monohydrate. On isolation, Form B's distinct crystalline forms are birefringent plates. Form B can be converted to form A in ethyl acetate at room temperature. Form B, by differential scanning calorimetry, undergoes loss of water at 76° C., slight recrystallization at 120° C., melt onset at 138.8° C., recrystallization and final melt onset at 159.9° C.

Dissolving Form A in methanol returned Form B which readily dried to a fairly stable polymorph. Bridging the polymorphs in ethyl acetate yielded Form A Bridging is a common term used in Chemical Microscopy and Crystallography for solution phase transformations, an experimental method often used to determine the lowest energy (most stable) crystalline form. Usually the crystalline forms are charged together in a variety of previously saturated solvents (saturated with the compound which provided the crystalline forms). After being slurred for a suitable period of time, the crystals are collected and examined to determine which crystalline form has prevailed. That crystalline form will be the lowest energy form under the experimental conditions.

Bridging of Form A with Form B yielded Form A from ethyl acetate and acetone and returned the original mixture of forms from the following solvents; tetrahydrofuran, ethyl acetate, cyclohexane, hexanes, acetonitrite and methyl ethyl ketone.

By stirring the less stable form, for example, the 8 Form, in ethyl acetate under ambient conditions results in the conversion to Form A.

Slurrying the anhydrous form or a mixture of forms in water yields the crystalline monohydrate which does not lose its water under drying conditions, e.g., at 45° C. in vacuo.

The A and B Forms of the citrate monohydrate possess valuable and nonobvious properties Since the Form A of the citrate monohydrate is hygroscopically stable, formulation problems due to weight changes of the active ingredient during tabletting or capsulation operations are alleviated. Form B has similar advantages at below about 85% relative humidity. Forms A and B and the anhydrous citrate can also be given by intravenous.

The effective dosage for the pharmaceutical composition of the citrate monohydrate depends on the intended route of administration, the indicator, the indication to be treated, and other factors such as age and weight of the subject. In the following dosage ranges, the terms "mg A" refers to milligrams of the monohydrate. A recommended range for oral dosing is 5–300 mgA/day, preferably 40–200 mgA/day more preferably 40–80 mgA/day, in single or divided doses. A recommended range for oral administration in oral forms such as pills or tablets is 2.5 mgA/day to 160 mgA/day and preferably 5–80 mgA/day. The stability of Form A. relative to all other forms is demonstrated by its lack of hygroscopicity and lower energy bridging and thermal conversions.

The following examples illustrate the methods and compounds of the present invention. It will be understood, however, that the invention is not limited to the specific Examples.

EXAMPLE I

Preparation of the Crystalline Citrate Monohydrate, Form A

The addition of a solution of 13.9 kg of citric acid (anhydrous, 99.5+%) in acetone (125 L) to a solution of 50 kg free base, in isopropyl alcohol (250 L). The clear solution was filtered, stirred and the acetone removed by distillation. The resulting mixture was stirred at ambient temperature until crystallization started and then granulated for an additional 16 hours. The white crystalline anhydrous citrate formed was collected by filtration and dried at 25° C. under vacuum (80% yield).

EXAMPLE II

Preparation of the Crystalline Citrate Monohydrate, Form B

A sample of Form A monohydrate was dissolved in methanol. The solution was stirred at room temperature and allow to concentrate with evaporation of the solvent. The resulting Form B was collected by filtration. An x-ray configuration, H nmr and combustion analyses were obtained confirming that the compound is Form B of the monohydrate.

We claim:

1. The crystalline forms of (2-Benzhydryl-1-azo-bicyclo[2.2.2]oct-3-yl)-(5-isopropyl-2-methoxybenzyl)-amine citrate having the formula

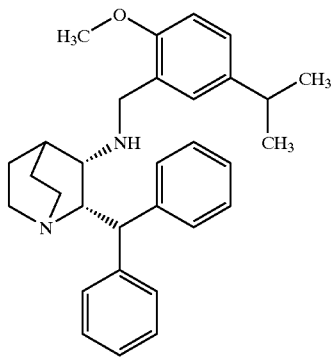

wherein said crystalline form is selected from the group consisting of
(a) a stable nonhygroscopic citrate anhydrous form exhibiting the X-ray powder diffraction pattern

| Peak No. | 1 | 2 | 3 | 4 | 5 | 6 | 7 | 8 | 9 |
|---|---|---|---|---|---|---|---|---|---|
| D space | 17.61 | 10.95 | 8.78 | 7.96 | 7.37 | 6.80 | 6.57 | 5.87 | 5.46 |

(b) a citrate monohydrate, Form A polymorph exhibiting the X-ray powder diffraction pattern

| Peak No. | 1 | 2 | 3 | 4 | 5 | 6 | 7 | 8 | 9 |
|---|---|---|---|---|---|---|---|---|---|
| D space | 17.74 | 10.93 | 9.65 | 8.25 | 6.71 | 5.98 | 5.67 | 5.45 | 4.83 | and
(c) A citrate monohydrate, Form B polymorph exhibiting the X-ray powder diffraction pattern

| Peak No. | 1 | 2 | 3 | 4 | 5 | 6 | 7 | 8 | 9 |
|---|---|---|---|---|---|---|---|---|---|
| D space | 12.3 | 11.3 | 6.5 | 6.9 | 5.9 | 4.3 | 4.1 | 3.5 | 3.2 |

2. The monohydrate polymorph according to claim 1 wherein Form A's crystalline habits are either acicular needles or plates.

3. The monohydrate polymorph Form B according to claim 1 wherein Form B's crystalline habits are crystalline plates.

4. The monohydrate polymorph Form B according to claim 1 obtained by concentrating a solution of the citrate monohydrate in methanol.

5. The anhydrous citrate salt according to claim 1 having a melt onset at about 159.9° C.

6. The anyhdrous citrate according to claim 1 which converts to a monohydrate in water.

7. The anyhdrous citrate according to claim 1 wherein hygroscopicity measurements demonstrated that about 1.11% wt/wt water was absorbed at about 90% relative humidity.

8. The anhydrous citrate according to claim 1 wherein it's crystalline habits are microcrystalline flakes.

9. The monohydrate polymorph form A according to claim 1 which is characterized by a melt onset at about 162.6° C.

10. The monohydrate polymorph form B according to claim 1 which is characterized by a melt onset at about 149° C. with degradation.

11. A pharmaceutical composition having substance P antagonist activity comprising at least one of the polymorphic Forms A or B according to claim 1, in an amount effective in the treatment of emesis and a pharmaceutically acceptable carrier.

12. A method of treating emesis which comprises administering to a subject in need of treatment an antiemetic effective amount of the polymorphic A Form of the compound according to claim 1.

13. A method of treating emesis which comprises administering to a subject in need of treatment an antiemetic effective amount of the polymorphic B Form of the compound according to claim 1.

14. A pharmaceutical composition having substance P antagonist activity comprising the anhydrous citrate according to claim 1, in an amount effective in the treatment of emesis, and a pharmaceutically acceptable carrier.

15. A method of treating emesis which comprises administering to a subject in need of treatment an antiemetic effective amount of the anhydrous citrate of the compound according to claim 1.

16. A method of making crystalline polymorphic Form A of (2-Benzhydryl-1-azo-bicyclo[2.2.2]oct-3-yl)-(5-isopropyl-2-methoxybenzyl)-amine citrate monohydrate comprising:
Dissolving anhydrous citrate in isopropyl alcohol and water; stirring the mixture overnight at room temperature; crystallizing the citrate monohydrate salt and collecting Form A by filtration; and drying at about 20 to 80° C. under vacuum.

17. The method of claim 16 wherein the synthesis is carried out under ambient conditions for about 1.5 to 72 hours.

18. The method of claim 16, wherein large crystals of Form A with a plate like habit are grown from an isopropanol/water solution and are grown with needle-like habit in acetone/diisopropyl ether/water.

19. A method of making crystalline polymorphic Form B of (2-Benzhydryl-1-azo-bicyclo[2.2.2]oct-3-yl)-(5-isopropyl-2-methoxybenzyl)-amine citrate monohydrate comprising:
Concentrating a solution of the citrate monohydrate in methanol at room temperature for about 48 to 72 hours.

* * * * *